United States Patent [19]

Muller et al.

[11] 4,410,242
[45] Oct. 18, 1983

[54] HIGH-PRECISION OPHTHALMOMETER WHICH IS INDEPENDENT OF DISTANCE

[75] Inventors: Ortwin Muller, Aalen; Kurt Schulz; Viktor Stopar, both of Oberkochen, all of Fed. Rep. of Germany

[73] Assignee: Carl Zeiss-Stiftung, Oberkochen, Fed. Rep. of Germany

[21] Appl. No.: 224,033

[22] Filed: Jan. 12, 1981

[30] Foreign Application Priority Data

Jan. 12, 1980 [DE] Fed. Rep. of Germany ....... 3000995

[51] Int. Cl.³ .............................................. A61B 3/10
[52] U.S. Cl. .................................................. 351/211
[58] Field of Search ..................... 351/6, 13, 205, 211

[56] References Cited

U.S. PATENT DOCUMENTS

| | | | |
|---|---|---|---|
| 2,733,634 | 2/1956 | Littmann et al. | 351/6 |
| 3,290,927 | 12/1966 | Gambs | 351/13 |
| 4,315,672 | 2/1982 | Müller | 351/13 |

*Primary Examiner*—F. L. Evans
*Attorney, Agent, or Firm*—Hopgood, Calimafde, Kalil, Blaustein & Judlowe

[57] ABSTRACT

An ophthalmometer measurement system employs two flat glass plates which move in opposite pivoted directions, to determine the distance between two mirror images on the cornea. The pivot suspensions and pivotal-displacement mechanism are free of play and account for a three-fold improvement in precision of measurement. Provision is made for adjustment to compensate for manufacturing tolerances, in glassplate thickness and mechanical-parts manufacture.

6 Claims, 4 Drawing Figures

4,410,242

HIGH-PRECISION OPHTHALMOMETER WHICH IS INDEPENDENT OF DISTANCE

BACKGROUND OF THE INVENTION

The invention relates to an ophthalmometer which is independent of distance, and which has a measurement mechanism for determining the distance between two mirror images (on the cornea) of measurement marks, specifically by means of two flat glass plates which are arranged one above the other and are swingable in opposite directions.

In ophthalmometers which measure the linear distance between cornea mirror images, the precision of the measurement value currently obtained is about ±0.05 mm. Present development work in this field is directed at greater precision.

A survey of the problems of ophthalmometry and of conventional ophthalmometers is given in an article by H. Littmann in the Süddeutsche Optikerzeitung II/53. An ophthalmometer which resulted from an analysis of the problems of ophthalmometry described therein has been described by H. Littmann in the Süddeutsche Optikerzeitung V/53.

BRIEF STATEMENT OF THE INVENTION

The object of the present invention is to develop a new ophthalmometer of high precision of measurement and which is suitable also for the fitting of contact lenses. The invention achieves this object, in the manner that, as a further development of the Helmholz ophthalmometer and of the variant shown in FIG. 5 of H. Littmann's article in the Süddeutsche Optikerzeitung II/53, the glass plates are mounted free of play, that their swinging motion is cam controlled, and that adjustment elements are provided which serve to compensate for manufacturing tolerances of the glass plates and of mechanical parts of the measurement mechanism.

One advantageous embodiment of the invention is characterized by the fact that the glass plates are supported fixed in cylindrical hubs which are rotatably supported via ball bearings in vee supports and that tension springs act on the hubs. Due to the tensed loading force of the springs, the result is obtained that the measurement hubs (and associated glass plates) move without play in the vee supports and can also pivot easily.

The glass plates are advisedly connected with levers which are guided by a transmission part or an intermediate member, specifically a follower tracking on a cam.

The advantage obtained with the invention resides in a realizable measurement precision of ±0.015 mm, i.e., at least a three-fold improvement.

DETAILED DESCRIPTION

One embodiment of the invention is shown in the drawing and will be described in further detail below. In the drawing.

Figure 1:
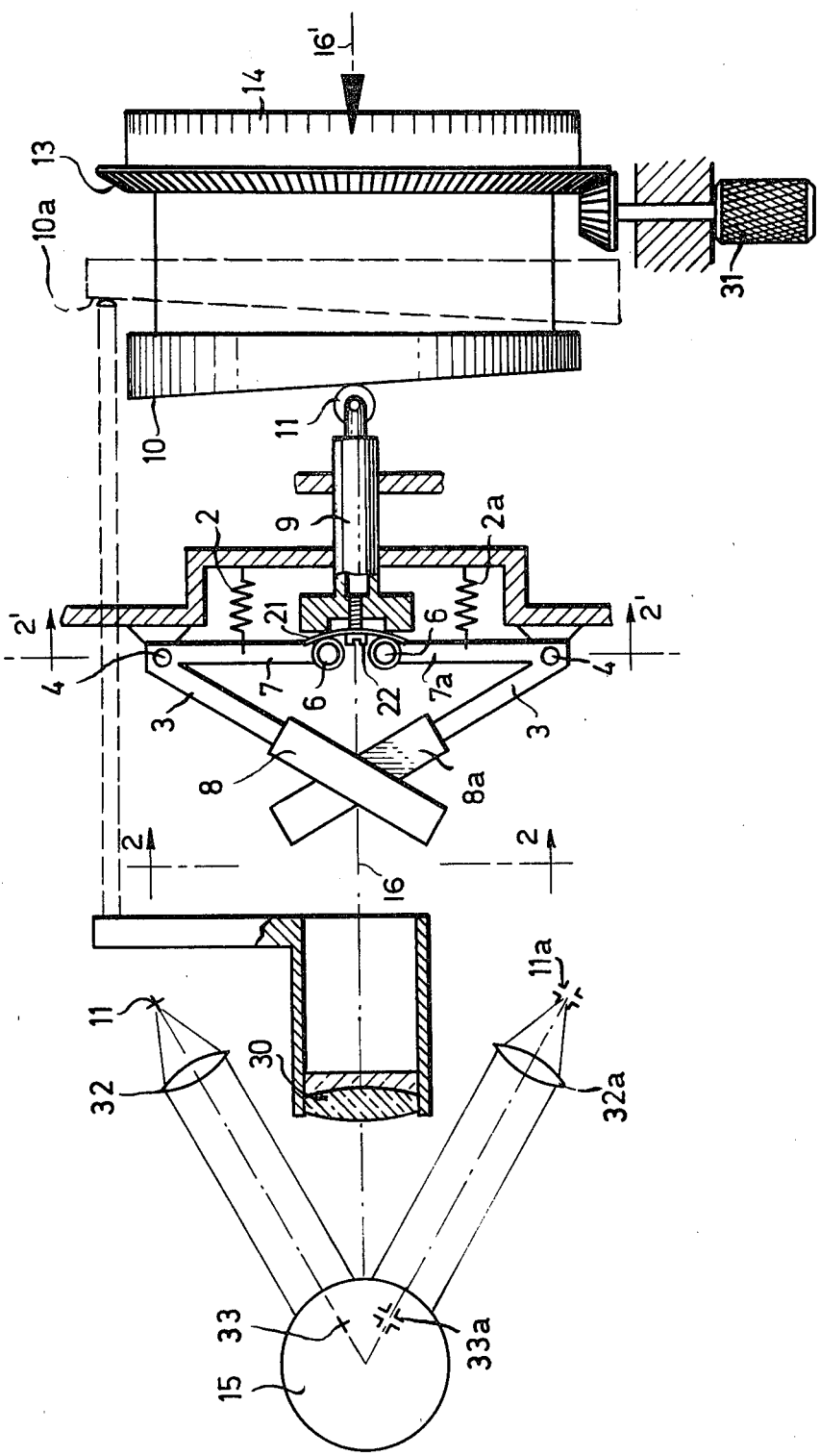
FIG. 1 is a diagrammatic sketch of ophthalmometer structure incorporating the invention.

In the diagrammatic sketch of FIG. 1, 15 is the eye of the patient. Measurement marks 11, 11a are imaged on the cornea of the eye of the patient as mirror images 33, 33a through collimators 32, 32a. The linear distance between these mirror images is measured by the Helmholtz method by means of two flat glass plates 8, 8a, which are arranged one above the other and are swingable in opposite directions; the glass plates 8, 8a will be understood to be part of an optical system including viewing means (not shown) located axially outward of the parts shown, but suggested by extension 16' of the central optical axis 16. From the diagrammatic sketch, it can be noted that by rotating an operating knob 31, annular structure in the form of drive wheel 13 and with it a scale ring 14 and an associated cam 10 are moved. The glass plates 8, 8a which are supported free of play via tension springs 2, 2a rotate, i.e., pivot, in response to cam-follower action via a ball bearing 11, an intermediate member 9 and levers 7, 7a. A lens 30 which is controlled via another cam 10a, serves to compensate for astigmatism.

Figure 2:
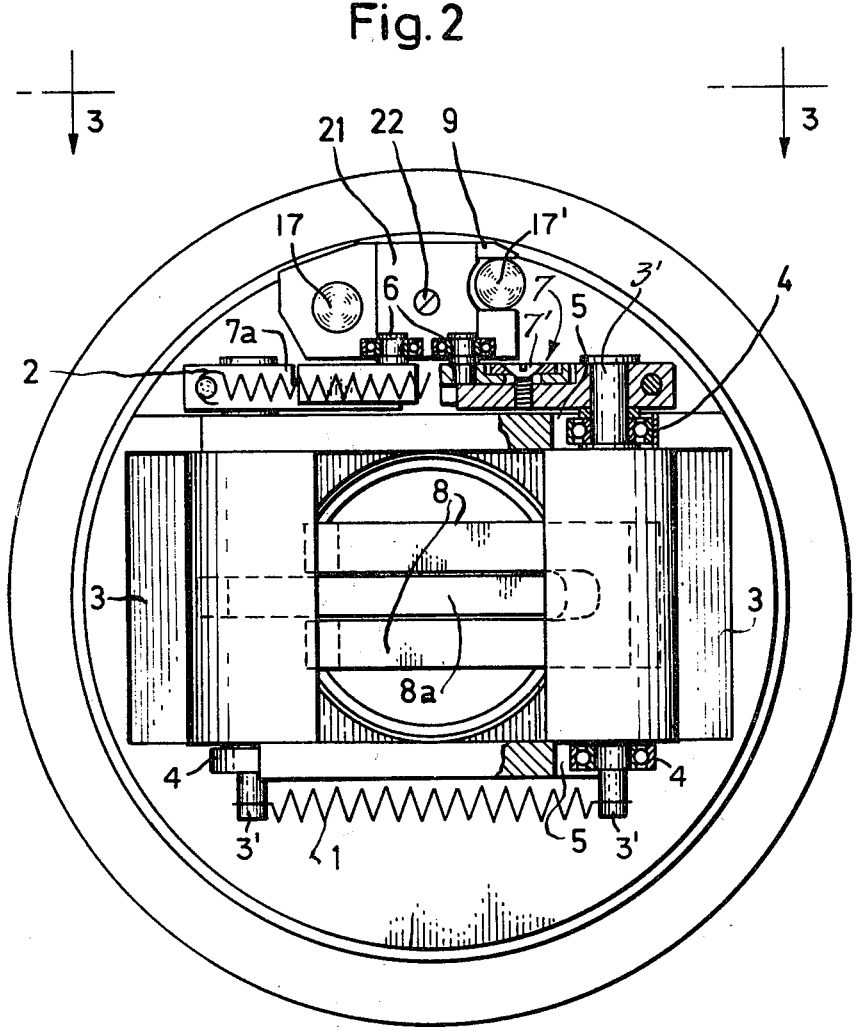
FIG. 2 is a transverse view, partly broken-away and in cross section through measurement mechanism of the invention, the view being taken at 2—2 and the section being taken at 2'—2' in FIG. 1.
Figure 3:
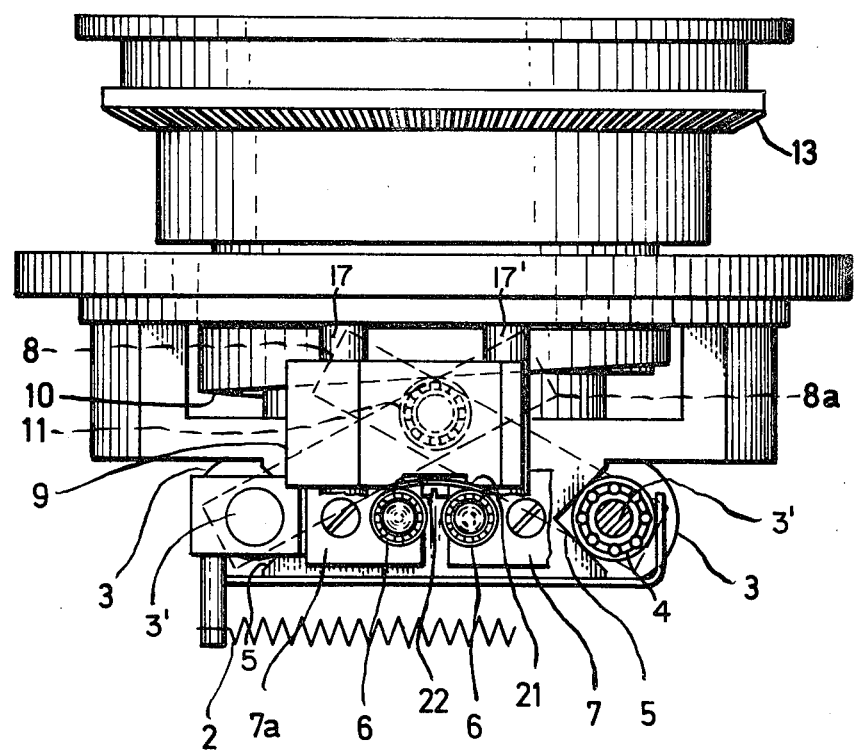
FIG. 3 is a side view of the measurement mechanism shown in FIG. 2, as seen from 3—3 in FIG. 2.
Figure 4:
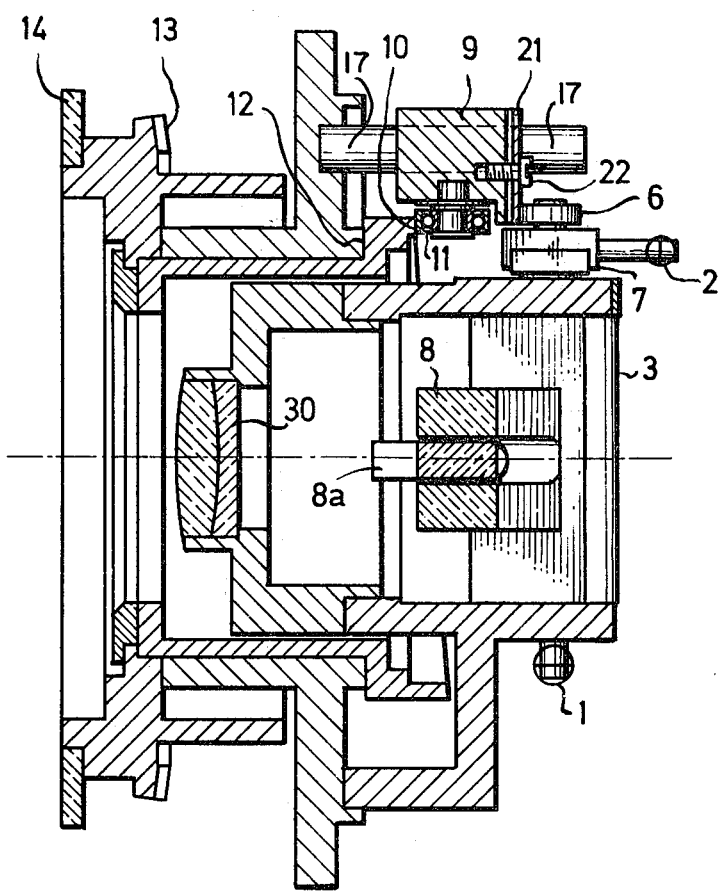
FIG. 4 is a longitudinal section through the measurement mechanism of FIGS. 2 and 3.

FIGS. 2, 3 and 4 show mechanism detail for the play-free support of the glass plates 8, 8a, as well as an adjustment element to compensate for manufacturing tolerances. The glass plates 8, 8a are supported fixed on cylindrical hubs 3 which in their turn are rotatably supported at their reduced ends 3' via ball bearings 4 in spaced fixed vee supports 5. Pivotal displacement of the glass plates is effected via levers 7 which are controlled from cam 10 by means of intermediate follower member 9; in FIGS. 2, 3 and 4 the intermediate member 9 is a block having longitudinally guided support in spaced parallel guide rods 17–17'. The tension springs 1, 2 load bearings 4 into their associated vee supports 5, and thereby achieve a mounting which is free of play, but hubs 3 and their associated plates 8, 8a, are nevertheless easily pivotable. In the case of tension spring 2, the point of spring attachment to each lever 7, 7a is located at radial offset from the axis of rotation, and therefore an additional torque is produced which, via each of the levers 7, 7a, and its ball-bearing follower roll 6, exerts an axially directed force on the intermediate member 9; in turn, this force on member 9 translates, via ball bearing 11, into pressure of cam 10 against the surface 12. In this way, the latter surface, which is important for the measurement, is also made free of play.

A stiffly compliant diaphragm 21, supported by and spanning a bifurcated end of intermediate member 9, provides the surfaces tracked by follower rolls 6; and a single set screw 22 adjustably connects diaphragm 21 to member 9 between the points of bifurcation support, thereby enabling a degree of adjustment (via set screw 22) of the effective length of member 9.

Furthermore, each ball bearing 6 can be displaceably supported on its associated lever 7, 7a as by dovetail and clamp structure 7' shown in FIG. 2. In such case, it is possible to change the effective length of the lever arm.

It is thus seen that, depending upon thickness of plate and cam slope at 10, the pivotal movement of glass plates 8, 8a is adjustable for a given rotation of the scale ring 14 (and of the associated drive gear 13 and cam 10).

What is claimed is:

1. An ophthalmometer with viewing means on an axis of viewing symmetry for radial orientation with respect to a cornea to be evaluated, said ophthalmometer having two mark-projection systems on axes symmetrically offset from and on opposite sides of the axis of viewing symmetry and adapted for radial orientation with respect to the cornea, said viewing means including two flat glass plates in lateral adjacency and pivotally mounted on spaced parallel axes for swing in equal and opposite angular directions from a plane normal to said axis of viewing symmetry, and means including a single cam for selectively varying the magnitude of equal and opposite angular swing with respect to said plane, said last-mentioned means comprising an intermediate follower block, a separate follower arm rigid to each glass plate and positioned to track follower-block movement, and spring means reacting between said plates at such offset from their respective pivot axes as to (1) resiliently load the pivoted support of said plates against radial play and (2) to apply follower-loading torque to both follower arms to thereby preload said block for continuous tracking of said cam.

2. The ophthalmometer of claim 1, in which the pivotal mounting of each of said plates is via ball-bearing means, and a fixed member having oppositely opening V-shaped recesses in which the ball-bearing means of the respective plates are engaged via preloading by said spring means.

3. The ophthalmometer of claim 1, in which each of said follower arms is adjustably variable as to its effective radius of follower-arm tracking of follower-block movement.

4. The ophthalmometer of claim 1, in which each of said follower arms carries a ball bearing which provides follower-arm tracking of follower-block movement.

5. The ophthalmometer of claim 4, in which the effective length of said follower block is adjustable.

6. The ophthalmometer of claim 4, in which said follower block has spaced bifurcations at the region of follower-arm tracking, a stiffly compliant diaphragm carried by said follower block and spanning the bifurcations, said follower-arm bearings tracking said diaphragm on the respective bifurcation sides thereof, and adjustable means reacting between said follower block and said diaphragm and at a location between said bifurcations for selectively varying deformation of said diaphragm to thereby provide fine adjustment of glass-plate swing to cam position.

* * * * *